United States Patent [19]

Fourmentin-Guilbert

[11] Patent Number: 5,612,181

[45] Date of Patent: Mar. 18, 1997

[54] METHOD FOR ARRANGING A POLYNUCLEOTIDE ON A SUBSTRATE FOR POINT-BY-POINT ANALYSIS OF THE BASES THEREOF

[76] Inventor: Jean E. R. Fourmentin-Guilbert, 84, avenue de la Republique, 93160 Noisy Le Grand, France

[21] Appl. No.: 282,627

[22] Filed: Jul. 29, 1994

Related U.S. Application Data

[63] Continuation-in-part of Ser. No. 845,918, Mar. 4, 1992, abandoned, which is a continuation-in-part of Ser. No. 541,530, Jun. 21, 1990, abandoned.

[30] Foreign Application Priority Data

Jun. 21, 1989 [FR] France .................................. 89 08284

[51] Int. Cl.⁶ .............................. C12Q 1/68; G01N 33/24
[52] U.S. Cl. ............................................... 435/6; 536/25.4
[58] Field of Search ................................. 435/6; 536/25.4

[56] References Cited

PUBLICATIONS

Journal of Vacuum Science & Technology/Section A vol. 6, No. 3, part II, "Atomic force microscopy and scanning tunneling microscopy with a combination atomic force microscope/scanning tunneling microscope".
Soviet Technical Physics Letters, vol. 13, No. 8, pp. 387–393.

*Primary Examiner*—Stephanie W. Zitomer
*Assistant Examiner*—Ethan C. Whisenant
*Attorney, Agent, or Firm*—Schweitzer Cornman & Gross

[57] ABSTRACT

The invention relates to a method for arranging a polynucleotide on a substrate for point-by-point analysis of each successive base. It includes in combination anchoring the polynucleotide towards one end to a precise location on a substrate, and stretching out the polynucleotide, in view of conducting a point-by-point analysis of the polynucleotide arranged on said surface.

11 Claims, 2 Drawing Sheets

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 1:

AGGTCGCCGC CCTAATTTAA TTAT    24

( 2 ) INFORMATION FOR SEQ ID NO: 2:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 2:

ACCGTT    6

METHOD FOR ARRANGING A POLYNUCLEOTIDE ON A SUBSTRATE FOR POINT-BY-POINT ANALYSIS OF THE BASES THEREOF

This application is a continuation-in-part of application Ser. No.07/845,918 filed on Mar. 4, 1992, itself a continuation-in-part of application Ser. No. 07/541,530 filed on Jun. 21, 1990, both abandoned.

FIELD OF THE INVENTION

The present invention concerns a method for arranging a polynucleotide on a substrate for a point-by-point analysis of the bases thereof.

BACKGROUND OF THE INVENTION

It is known that the genetic information of each living creature, its genome, is contained in its chromosomes, which are made up of long chains of nucleic acids, namely DNA and RNA.

All these nucleic acids are therefore constituted by a chaining of nucleotides having either a purine base (adenine or guanine) or a pyrimidine base (cytosine or uracil in RNA and cytosine or thymine in DNA).

Point-by-point analysis of polynucleotides deposited on a substrate is considered to be a promising tool for analysis of the shape of each successive purine or pyrimidine base. Shape reconstruction and identification of said bases can be envisaged. But problems, including control of the method of arranging and localizing polynucleotides on a substrate for accurate analysis of the successive bases thereof, still have to be solved.

One attempt at such a method is described by LEE et al in SCIENCE, vol 244 (1989) pp 475–477.

According to this reference, bundles of molecules are deposited freely in droplets on a substrate and a scanning tunnel effect microscope is used to image tertiary (helical) DNA structure.

SUMMARY OF THE INVENTION

The invention provides a method for arranging a polynucleotide sample on the surface of a substrate for a point-by-point analysis of each successive base of said polynucleotide, said point-by-point analysis being performing by scanning said surface by means of a probe which is part of a tunnel effect microscope and which is capable of detecting a difference of level with respect to the surface of less than one atomic diameter, comprising:

positionning said polynucleotide by anchoring said polynucleotide towards a first extremity thereof to the substrate at a precise location on said substrate, and stretching out said anchored polynucleotide by performing at least one step selected from the group consisting of:

(i) placing the said anchored polynucleotide in a current of a fluid, and (ii) applying an electric field.

The anchored polynucleotide is thus stretched out in the direction of said current of fluid and/or in the direction of said electric field.

Having disposed (anchored and unravelled) the polynucleotide on the substrate so as to allow scanning, the method according to the invention thus makes it possible point-by-point analysis and direct gathering of (e.g. topological and/or spectroscopic) data on each successive base of the fragment to be analyzed.

The point-by-point analysis provides data or information that may be stored for instance in a computer memory.

The distinction between a purine nucleus and a pyrimidine nucleus can be made because a purine nucleus appears in the shape of a double cycle of nine atoms while the pyrimidine nucleus in the shape of a cycle of six atoms.

The thymine bass are distinguished from the cytosine bases notably by the presence, in the former, of a methyl substituent Likewise, the guanine bases are distinguished from the adenine bases notably by the presence, in the former, of a nitrogen substituent located at $C_2$.

In order to make this distinction easier, one can add a characteristic marker on one of the two purine type bases and on one of the two pyrimidine type bases of the polynucleotide to be analyzed.

In the case of a deoxyribonucleic acid fragment, it will thus be possible to mark either the adenine bases or the thymine bases on the one hand, and either the cytosine bases or the guanine bases on the other.

Alternatively this distinction may be achieved by measuring charge density distributions using, for example, a near field microscope.

Charge density distribution is characteristic of individual pyrimidines and purines, the difference in this parameter at $C_4$ between thymine and cytosine being −0.47 eV with that at $C_6$ between adenosine and guanine also being −0.47 eV.

The point-by-point analysis mentioned above may be performed by scanning the said surface with a resolution of less than one atomic diameter by means of a probe, as in for example near field microscopy using preferably a tunnel-effect or atomic force microscope.

The word "probe" in this context has its usual meaning, i.e. an instrument or part of an instrument that closely examines a subject. It is not to be confused with the use of the word in the gene manipulation art.

The tunnel-effect microscope, or STM, is known (G. Binnig et al., Phys. Rev. Lett. 50, 120, 1983; and G. Binnig et al., in "Trends in Physics", edited by J. Janta and J. Pantoflicek, European Physical Society, The Hague, 1984, pp. 38–46). However, we shall briefly review its principle of operation.

If a sufficiently fine probe is brought into the immediate proximity of a surface and if a potential difference is applied between the probe and the surface, an electric current is created by the tunnel effect, this electric current depending very greatly on the electron density at the level of the tip of the probe, i.e., on the distance between this point and the surface.

The tunnel effect microscope, therefore, consists of producing an X and Y axis scan of the surface to be analyzed by mans of a probe, for example by means of piezoelectric devices, and, during this scan, of moving the probe vertically on the Z axis, also by means of a piezoelectric device, so as to obtain a current of constant intensity. The servo voltage for obtaining this constant current is therefore representative of the differences in level (Z) encountered during the scan.

Differences in level of the order of one atomic diameter with respect to the substrate surface can be detected. Values of Z thus provide topographical data for base identification.

Topographical analysis may be substituted or preferably supplemented by a spectroscopic analysis whereby at each X, Y point scanned and at constant servo voltage in the Z axis, the tunnel current variation ($\Delta I_t$) caused by varying the potential difference between probe and substrate ($\Delta U_p$) are measured. The ratio, $\alpha$, of $\Delta I_t$ to $\Delta U_p$ provides spectroscopic data identifying the bases.

The data gathered constitute the (electronic) signature of the bases and may be interpreted e.g. by a computer preferably by shape reconstruction.

The expression "shape reconstruction" means processing the data gathered so as to derive parameters characteristic of the shape of each base. These parameters might be used to create an image of the shape of each base by conventional imaging techniques.

Such an image may remain virtual in that it exists only in the memory of a computer or it may be visualised.

Those skilled in the art will understand that an Atomic Force Microscope or a Photon Scanning Tunnelling Microscope can also be used.

It is, of course, possible to use the probe to scan the entire substrate on which the fragment to be scanned is placed.

However, to obtain a faster analysis it is possible to control the X and Y scan so as to follow this fragment, for example by stopping the primary scan at a certain distance such as 100 nm or 1 micron after the beginning of each sweep over the surface of the substrate, which can be a crystal having a substantially flawless surface.

In order to know its position, it is also more simply possible to arrange the fragment in a groove formed in the substrate and to limit the scan to the width of this groove.

The polynucleotide can particularly be arranged on the substrate by making it migrate by potential gradient in a solution in which this substrate is immersed.

In this case, in order to stretch out the polynucleotide to facilitate its study, one of its extremities ("first end") is anchored at a point on the substrate, for example by grafting onto this extremity, and onto the substrate, interactive ("first" and "second") functional groups which carry for instance electrostatic charges or are capable of forming a covalent bond.

Preferably in both cases the first functional group is grafted to the extremity of a predetermined sequence, itself synthesized at the first end of the polynucleotide proper which is to be sequenced.

A terminal group (e.g. functional group, molecule or macromolecule e.g. of opposite charge) can also be grafted onto the free end ("second end") of the anchored polynucleotide to facilitate elongation.

It is also possible to perform the elongation and migration of the polynucleotide by placing it in a moving fluid whose velocity is controlled. The migration can be enhanced by the presence of the above mentioned molecule grafted onto the free end of the polynucleotide. Such a molecule preferably has a frontal surface area of approximately 10 nm$^2$.

The fluid velocity depends on the fluid used. It will be greater with a gas, for example, such as air, than with a liquid such as water, for example.

The aim is to give the polynucleotide sufficient kinetic energy to stretch out the polynucleotide but minimize the risk of breaking it up.

The polynucleotide may be placed in a groove on the substrate that will serve for its analysis.

One of the ends of the polynucleotide is anchored, for example to the substrate. The groove may be covered with a slide cover (cover glass) so as to create a channel for the flow of the fluid. A funnel-shaped article having an opening to permit the passage of the fluid may be placed at the entrance of the channel to permit the injection of the fluid.

The fluid is then injected for a sufficient period of time to obtain the desired elongation. Once the desired elongation is achieved, the funnel-shaped article and the slide cover are removed.

It is equally possible to bring about the elongation of the polynucleotide by centrifugation. This again can be enhanced by grafting a macromolecule onto the second (free) end of the anchored polynucleotide.

A single-strand polynucleotide will be used preferentially for the sequencing to facilitate study.

For this purpose one can begin with a double-stranded polynucleotide and, after anchoring down its extremity, the two strands can be separated, one of the strands can be cut away at its extremity, and the migration of the latter strand can be watched until it is completely removed from the strand that remains anchored.

The synthesized predetermined sequence between the end of the polynucleotide proper and the first functional group serves a certain number of functions.

First of all, it permits the recognition of the reading direction from 5' toward 3' or the reverse.

Moreover, it permits the identification of the first meaningful nucleotide of the strand being read.

It also permits a covalent bond with the first functional group grafted onto its extremity.

When starting out from a double-stranded polynucleotide, it furthermore permits a specific severance of one of the strands with a suitable restriction enzyme.

Lastly, it permits a certain flexibility between the functional group and the polynucleotide.

The polynucleotide, optionally comprising the predetermined synthesized sequence and the first functional group, can be either deposited on the substrate in the form of a solution as a microdrop at a precise location by means of a micropipette, and then drawn towards the anchoring site on the substrate, or the interactive functional groups can be brought into contact by soaking the substrate in a solution containing a great number of identical polynucleotides.

In the first case the microdrop may be placed e.g. in a groove a few microns wide with a depth of about 100 nanometers.

Preferably, the groove is filled with a conductive solution. By placing an electrode at each end of the groove, and connecting the electrodes to a voltage source, an electric field of suitable polarity my be established in the solution between the electrodes.

Under the effect of the electric field, the polynucleotide, will migrate toward the pole of the sign opposite to the polarization of the polynucleotide.

When the barrier constituted by the second functional group (which may be an electrostatic charge) attached to the substrate is passed, a first functional group attached to the polynucleotide forms an electrostatic or covalent bond, and consequently remains attached to the second functional group. After this attachment, the remainder of the polynucleotide continues to stretch out under the effect of the electrical field.

Once the elongation is completed, and if the starting polynucleotide was double-stranded, heat may be applied to denature the bonds of this double strand.

A restriction enzyme specific for one strand of the attaching chain of predetermined sequence may be also employed to sever one of the strands. By maintaining the potential difference, the migration of the severed single-strand polynucleotide can thus be continued until it is completely removed from the single strand remaining attached to the substrate.

In the case where the substrate is soaked in a solution containing a great number of identical polynucleotides, the same anchoring and elongation (i.e. stretching out) methods can be used, but it may be necessary to multiply beforehand the polynucleotide that is to be sequenced in order to obtain a reasonable probability of the attachment of the second functional group bound to the substrate to the first functional group on the polynucleotide. Multiple attachment sites may be provided on the substrate to anchor a plurality of identical polynucleotides.

In both cases, a transverse electric field may also be applied in order to flatten the polynucleotides against the substrate.

In both cases, the solution may be then slowly evaporated, either by microsuction of the solvent, or by heating, or by using beth methods.

The present invention also has as its subject matter an automatic device for shape analysis of a polynucleotide such as a gene, characterized by the fact that it comprises, in combination, a substrate whose surface roughness is of the order of one atomic diameter, means for the point-by-point analysis of the said surface with a resolution better than one atomic diameter, and optionally means for creating an image of the successive bases of the said polynucleotide on the basis of the data from the analysis, means for studying the said image and means for storing in memory the information thus obtained.

The means of analysis can in particular include a probe adapted to detect a difference in level on the said surface amounting to less than one atomic diameter, and scanning means for causing the said probe to scan the said surface with a resolution better than one atomic diameter, for example the probe and the scanning means of a tunnel-effect microscope.

Of course, coarser analyzing means, such as the same microscope suitably adjusted, having for example a resolution of the order of ten nanometers, can be used primarily for locating the polynucleotide on the substrate.

The substrate is preferably a crystalline substrate such as graphite or gold.

The substrate can also include markings engraved at predetermined intervals. Such markings are particularly preferred in conjunction with the above mentioned groove in which case they are engraved along the groove.

These marks will make it possible to perform several scan cycles successively, each cycle covering a given length of the substrate or groove, and to reset the scanner from one cycle to another.

Furthermore, the marks allow rapid localisation of a deposited micro-drop and of functional groups on the substrate (and therefore where the polynucleotide is anchored) and thus permit easy localisation of the portion being scanned or rescanned. The markings are equivalent to the grid used in electron microscope imaging.

The substrate can also include means for the attachment and straightening out of the polynucleotide to be analyzed.

The point-by-point analysis can be followed by a step of shape reconstruction in a processing unit designed to reconstruct the surface in three dimensions, and means for determining three-dimensional shapes.

Methods are known which permit reconstruction of a surface in three dimensions on the basis of the coordinates in these three dimensions of a set of points on this surface. Also known are means for determining three-dimensional shapes (the pentose and base sub-units remain in a rigid, well-determined spatial configuration).

The means for the reconstruction and identification of shape may include a processing unit desired to reconstruct a planar image of the surface, image processing means and means for the study of images.

In this case, a two-dimensional image of the surface may be consequently formed on the basis of the data from the analysis of the surface and of the polynucleotide which it bears (this, of course, can be created only from a matrix of information pixels in the memory of a computer), this image is processed so as to isolate the atoms of the successive bases of the polynucleotide by eliminating the atoms of the substrate as well as those of the deoxyribose groups (or ribose groups in the case of RNA), and those of the phosphoryl groups. When the images of the successive bases have thus been reconstructed, they can be analyzed automatically.

In view of the above description, it will be understood that in a particular embodiment of the claimed method, the polynucleotide to be analyzed may bear at one of its extremities (the first extremity) a functional group (first functional group) while the substrate bears at a precise location, i.e. at a point of the substrate which is localisable, a second functional group. The first and second functional groups mutually interact when brought into contact, and said interaction results in anchoring the polynucleotide to the substrate. The functional groups may interact electrostatically or may interact to form a covalent bond.

The first functional group may also be introduced through an intermediate spacer arm, an extremity of which is coupled to said first extremity while the other extremity of the spacer arm bears the said first functional group.

When the polynucleotide is initially double-stranded, a first functional group may be grafted on at least one of the two strands at said first extremity.

The functional groups interacting electrostatically include carboxylate or phosphate ions, —S—, —SS$^{31}$, AuCl$_4$$^{31}$ cations such as ammonium or magnesium cations.

The electrostatically-interacting functional groups may be introduced in a known manner.

The functional groups capable of mutually interacting to form a covalent bond may comprise any such couple of functional groups known in the art of chemistry to so interact. These couples of funtional groups include those which react with formation of an ester bond, an amide bond, an ether bond, a thioether bond, etc . . .

The functional groups may also interact by affinity, such as the well known biotin-avidin complex.

Alternative methods for anchoring the polynucleotide at a point on the substrate which is easily localisable include indirect anchoring in a known manner to a magnetic microbead which is then maintained at a precise location on a substrate with the aid of a magnet.

The use of magnetic microbeads has been described e.g. in the following publications: John B. Jarp J., Act. Pathology Microbiology Immunology Scand. Sect. C 1988, 27 No. 7: 1631–1635; as well as technical documents of commercial suppliers DYNAL and SERADYN.

As noted above, a predetermined nucleotidic sequence may be synthesized at one end of the polynucleotide to be analyzed. In this case, the polynucleotide to be anchored comprises the polynucleotide to be analyzed + the added sequence and, the extremity to be anchored (i.e. the above-mentioned first extremity) is the free end of the so-grafted predetermined sequence. When the polynucleotide is initially double-stranded, said predetermined nucleotidic sequence may be chosen e.g. among those sequences which allow specific severance of one of the strands under action of a restriction enzyme, and in this case the method includes a step of causing a suitable restriction enzyme to act, in a manner known per se, on the anchored double-stranded polynucleotide to render it single-stranded.

The restriction enzymes which may be used include EcoR1 which, in a 50 mM Tris Hcl 0.1M Nacl solution free from magnesium ions, is capable of severing only one strand of a double strand, between G and AATT.

The predetermined sequence to be grafted at one extremity of the polynucleotide to be analyzed may be synthesized according to known methods.

It is also possible to obtain said predetermined sequences in the form of commercial oligonucleotides containing a sequence recognized by a restriction enzyme and to ligate, by conventional methods, said commercial oligonucleotides to the polynucleotide to be studied.

A description will now be given by way of nonrestrictive example of one particular embodiment of the invention, in conjunction with the appended drawings wherein:

FIG. 1 represents a tunnel-effect microscope generally indicated at 1. This microscope includes a probe 2 consisting of a needle whose end forms a monoatomic point, and whose movements are achieved by means of piezoelectric crystals $P_X$, $P_Y$ and $P_Z$.

The crystals $P_X$ and $P_Y$ are controlled respectively by an X scanning unit 3 and a Y scanning unit 4.

Figure 1:
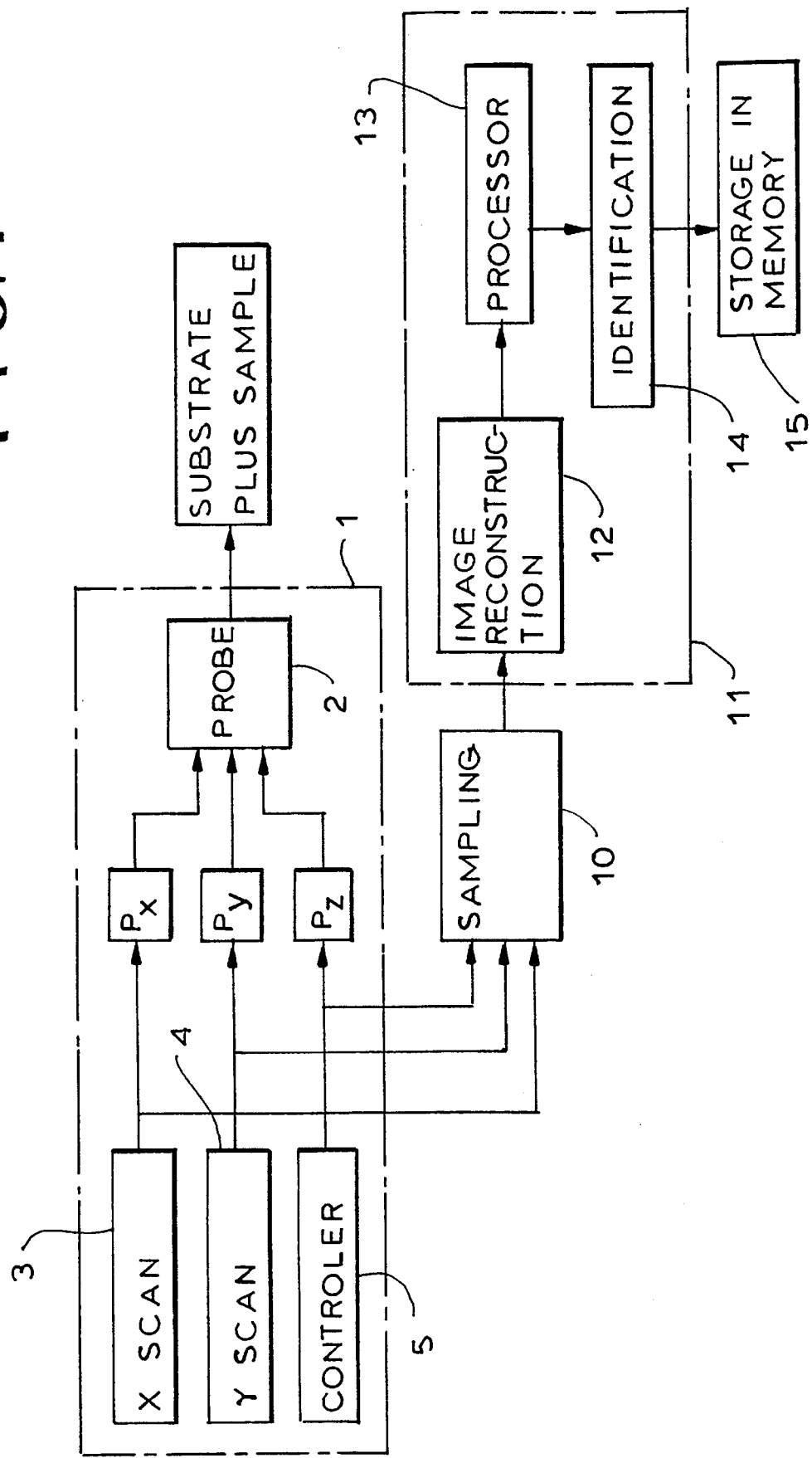
FIG. 1 is an overall diagram of the device according to the invention.
Figure 2:
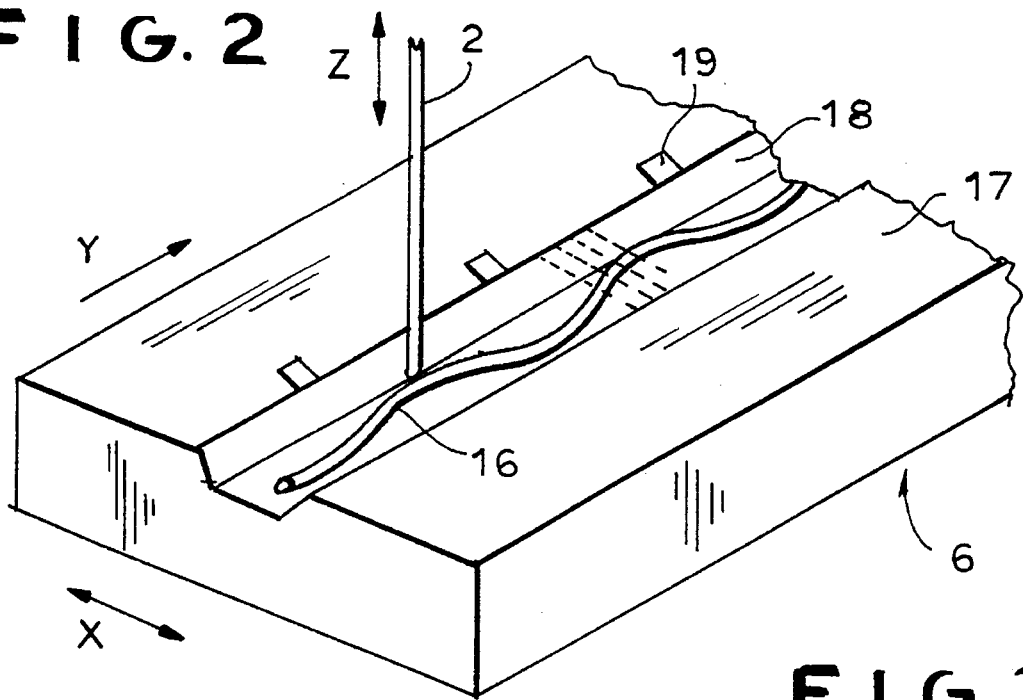
FIG. 2 is a perspective representation of the substrate, the polynucleotide and the probe.
Figure 3:
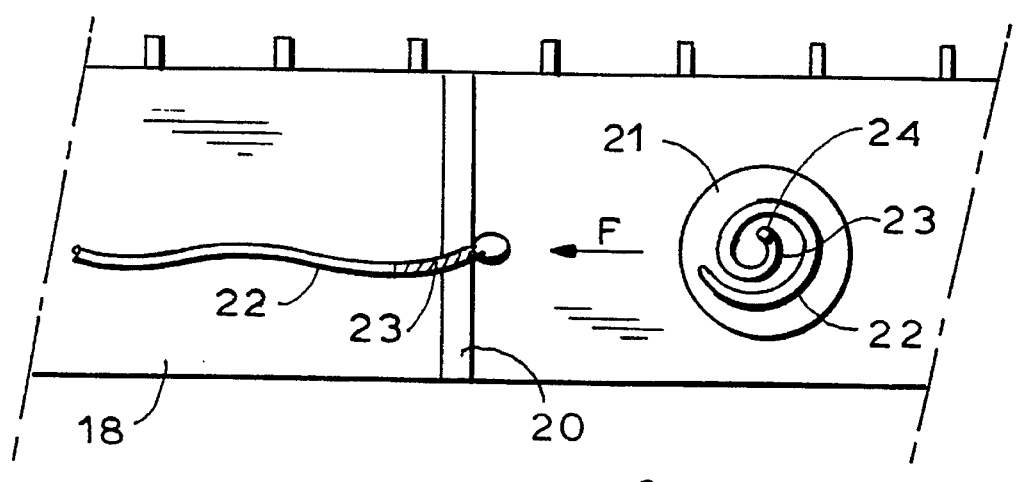
FIG. 3 is a top view, greatly enlarged, of the groove in the substrate and of the polynucleotide.

The piezoelectric crystal $P_Z$ is servo-controlled by a controller 5 tending to maintain the constancy of the current flowing between the probe 2 and the substrate/polynucleotide 16 (FIG. 2) when a constant potential difference is applied between this probe and the substrate/polynucleotide.

Simultaneously, and at each X, Y position scanned, it is possible to hold distance Z constant by applying to crystal Pz a constant servo-voltage while varying the potential difference ($U_p$) between probe and substrate/polynucleotide. This in turn causes the tunnel current ($I_t$) to vary.

The values of α and Z thus obtained and the coordinates X, and Y of the tip of the probe 2 are sampled in a sampler 10 whose output is applied to the input of a processing unit 11.

The processing unit 11 is composed essentially of an image reconstruction module 12, an image processing module, and an analyzing module 14.

The module 12 makes it possible on the basis of the data sampled to reconstruct a two-dimensional image of the surface of the substrate and of the fragment of nucleic acid which is deposited thereon. Where the data sampled includes spectroscopic data, the image obtained is no longer truly representative of the surface of the substrate and instead represents a pseudo-image of each base analysed.

The processing unit 13 eliminates from the image thus obtained the image of the atoms of the substrate and of the atoms of the phosphoryl and ribose or deoxyribose groups, so that all that will be left on the image is the purine or pyrimidine nuclei as well as the atoms of the marker that may have been used in order to distinguish the two purine type bases from one another, as well as the two pyrimidine-type bases. This can be brought about by means of image processing programs such as exist in many technical fields.

Lastly, the analysis module 14 serves to analyze each base in succession.

The result thus obtained is entered in a memory unit 15 which consequently contains, at the end of the operation, the sequence of the bases of the polynucleotide sequenced by the method of the invention.

In the present case, the substrate 6 consists of a graphite crystal obtained, for example, by epitaxy, so that its surface 17 has no defects.

A groove 18 is formed on the surface 17 of the substrate 6 by techniques known in microelectronics.

Furthermore, marks 19 are engraved at regular intervals along the groove, also by known means.

The substrate furthermore has a well (not shown) at each end of the groove 18 for the purpose of immersing two electrodes permitting the creation of an electrical field in a solution contained in these wells and the groove.

The groove can have, for example, a width of about 2 microns and a depth of about 100 nanometers.

Lastly, the bottom of the groove is doped in the form of a strip perpendicular to the groove, having a width of about 100 nanometers, either of an electrostatic charge, or of functional groups having a strong reactivity with the functional groups grafted onto the end of the polynucleotide.

The electrostatic charge can be obtained either by a removal of electrons performed directly with a tunnel-effect microscope, or by depositing a molecular layer of one molecule, or depositing a charged macromocule, or of a mass of charged molecules.

For example, a monomolecular layer may be deposited, having the general form $CH_3—(CH_2)_{n-2}—COOH$, n being between 16 and 22, this monomolecular layer receiving surface-inserted functional groups (Langmuir-Blotgett technique).

A microdrop 21 is deposited in the groove 18 upstream from the barrier 20 in the direction of migration, in a solution contained in the groove.

This microdrop contains the polynucleotide to be sequenced 22, onto one end of which a fragment 23 of known sequence has been synthesized, and a positively charged functional group 24.

On account of the electrical field prevailing in the solution, the microdrop moves toward the barrier 20 in the groove, which, in the present case, is positively charged.

The group 24 is consequently held upstream from the barrier 20, the polynucleotide 22 continuing to stretch out downstream from this barrier.

If the polynucleotide is double-stranded, the procedure described above will be followed, in order to separate the two strands, and the solution contained in the groove will be evaporated.

Then the tip of the probe 2 is brought close to the bottom of the groove, and with this probe a primary scan on the X axis is performed over the width of the groove 18, and a secondary scan along the groove on the Y axis while keeping the distance between the tip of the probe 2 and the surface constant.

Figure 4:
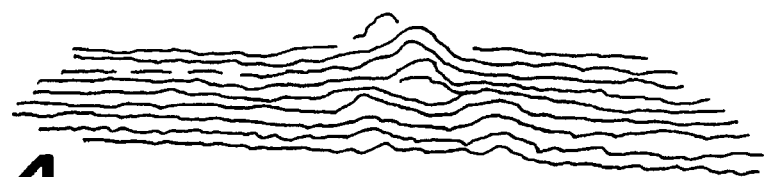
FIG. 4 represents the record made by the tunnel-effect microscope.

Then a recording of the type represented in FIG. 4 may be obtained.

The values of X, Y and Z are sampled as the scan progresses, with a precision which, in the present state of the art, can be of the order of 0.1 angstrom, and the data thus obtained will be entered in the processing unit.

Figure 5:
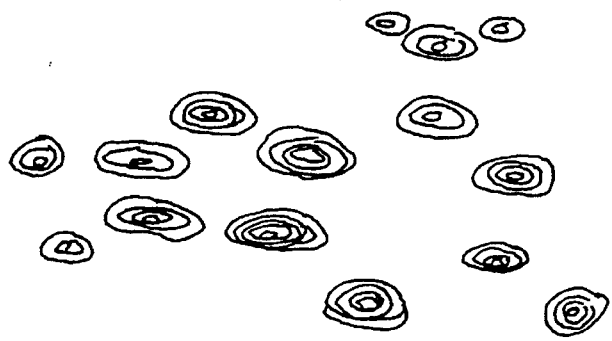
FIG. 5 represents the image obtained after processing the signal obtained from the microscope.

After processing, an image will be obtained like the one represented in FIG. 5, which may be analyzed by the share analysis module 14. A similar pseudo-image can be obtained from spectroscopic data.

The method of the invention therefore will permit an extremely fast analysis of a long fragment of nucleic acid. The processing of the data gathered can be performed in real time, in which case, with the present-day shape recognizing techniques, the scan must be relatively slow, but another possibility consists in performing the processing only at a later time, in which case the analysis can be performed at great speed.

Lastly, it will be noted that this process is nondestructive, and that therefore as many tests as desired can be made on the same sample.

EXAMPLES

Example 1: Deposition in a Groove a) Preparation of biotinylated DNA,

To 40 micrograms of Lambda phage DNA (GIBCO BRL) dissolved in 10 mM Tris HCl, 1 mM EDTA, 10 mM NaCl buffer, were added 10 micrograms of the following oligonucleotide:

3' AbTATTAATTTAATCCCGCCGCTGGA 5' (Seq. No.1)

where Ab is biotinylated A.

Said oligonucleotide, supplied by GENSET (France) has a sequence which is complementary to the COSL single strand end of lambda phage.

The mixture was heated up to 65° C. for 2 minutes and then slowly cooled to 20° C. After hybridization, a ligation reaction was carried out by mixing in an Eppendorf tube:

228 microliters of highly purified water (R>18 Megohms/cm), 80 microliters of ligation buffer 5X, 72 microliters of the DNA+oligo mixture, 20 microliters of ligase (1 U/µl), and by keeping the mixture during 24 h at 20° C.

The ligase was ligase T4 supplied by GIBCO BRL with the 5X ligation buffer.

For eliminating free biotinylated oligonucleotide, 8 µl of a 3M sodium acetate aqueous solution (pH 5.2) and 240 µl of isopropanol were added. After mixing, the mixture was let to settle a few minutes. The supernatant was eliminated and the precipitate was resuspended in 400 µl of TE buffer (TE buffer=10 mM Tris HCl–GIBCO Ref. 540+1 mM EDTA)

After 24 hours at 4° C. the linkage was checked by electrophoresis on 0.8% agarose gel.

b) Fluorescent labeling

In an Eppendorf tube, there were added:

6 µl of DMSO—$H_2O$(¼ v.v)

3 µl of YOYO fluorescent dye ($10^{-10}$ mol/ml in the same buffer)

1 µl of the suspension containing the biotinylated lambda phage DNA (1 ng/µl in buffer TE)

The YOYO fluorescent dye is supplied by "MOLECULAR PROBES INC."

The DMSO—$H_2O$ is supplied by ALDRICH (Dimethyl sulfoxid).

The mixture was agitated for 45 min. under nitrogen in the dark.

c) Preparation of support

The surface of freshly cleaved HOPG (Highly Orientated Pyrolitic Graphite—Union Carbide) was coated with a Langmuir-Blodgett film composed of an equimolar solution of imidazole and TIP (Tetraphenyl porphyrin) (Thin Solid films 1985-82-711 C; C. Lecomte and A. Barraud). A 2 µm-wide groove was engraved in the coating with the tip of a STM PROBE. The STM is equipped with a video camera for visualization of the tip-surface space.

The groove was treated with an aqueous acetic acid $CrO_3$ solution and rinsed.

A L.O.P.C. solution (biotinylated Lyso Octanoylglycero Phosphoryl Choline, bonded to streptavidin ) was prepared; references: W. Heckl, J. Vac. Sci. Technol., 1988, $A_6$ (2)-368 and Wilcheck and A. Bayer, Analytical Biochemistry, 171.1–32 (1988). A nanodrop of said solution was taken with the tip of a STM probe and deposited in the central region of the groove.

d) Deposit and stretching of DNA

Similarly, a nanodrop of the DNA solution was placed at a different location in the groove.

An ITO coated (50 nm) circular coverglass (diameter 3 cm) was partly coated with a stick film, in the form of lateral strips having a thickness of about 100 µm. The graphite support (8×8 mm) was placed on the sticky coating of the coverglass, and the whole was placed in the central compartment of a two-compartment cylindrical cell having a central 2 cm high vertical wall separating the two compartments.

The first compartment was filled with a TBE 0.5 X buffer+4% mercaptoethanol (45 mM Tris base+45 mM boric acid +500 mM EDTA), pH8, thus creating between the support and coverglass a liquid stream through the groove towards the second compartment. The liquid stream brings the DNA drop into contact with the central drop containing streptavidin (whereby one strand of the DNA becomes fixed through biotin-avidin attachment) and then the DNA strand is caused to be stretched out downstream by the circulating liquid.

The buffer in the first compartment was supplemented with NaOH up to 0.4M and 2% formaldehyde and progressively heated to 65° C. in order to denature the DNA, thus allowing the non-attached strand to be dragged along by the circulating fluid.

The cell was equipped with a fluorescence microscope allowing visualization of the central part of the groove.

It was observed that the length of the remaining stretched single strand was about three times the length of the originally fixed double strand.

While maintaining the fluid stream, an electric field was applied between the support and the ITO-coated coverglass; a 5 V direct current was applied for 10 seconds, thus causing the DNA strand to flatten against the support.

After washing with a slow stream of highly purified water, the support was dried by slow heating up to 40° C.

The stretched out and fixed DNA, localized in the center of the groove, was then ready for STM analysis.

Example 2 a) Preparation of biotinylated DNA

Said preparation was carried out as in Example 1.

b) Fixation of DNA on magnetic microbeads

The magnetic beads DYNABEADS, coated with streptavidin, were supplied by DYNAL France, as a suspension containing $6.10^8$ beads/$cm^3$. The beads (20 µl) were washed three times with 10 µl of 1M NaCl TE buffer as recommended by the supplier. Then 1 µl of biotinylated DNA containing 50 ng DNA was added.

The amounts of reactants were calculated in order to obtain an average of 1 DNA molecule linked to 1 bead through biotin-streptavidin linkage.

After incubating the mixture for 30 minutes at 45° C. with gentle stirring, the beads were washed with TE buffer and then resuspended in 20 µl TE buffer.

c) Fluorescent labeling

As in Example 1.

11 d) Preparation of support

The support was a gold monocrystal, polished according to plane 001 and annealed under vacuum for 24 hours at 550° C.

The 4×4 mm gold support was glued on a 8×8 mm stainless steel plate having engraved marks.

e) Deposit and stretching of DNA

A microdrop (1 μl) of the beads suspension, containing fluorescent DNA anchored to the beads, was deposited onto the center of the gold support.

The support was then placed in the two-compartment cell as described in Example 1. The cell was further equipped with a magnet having a sharp tip positioned vertically under the center of the support. The position of the magnet tip thus determined the location of the magnetic beads on the gold support.

The DNA was streched out with a circulating liquid, then denatured and stretched out as a single strand with the aid of the circulating liquid and electric field, as described in Example 1.

f) STM analysis

With the help of the fluorescence microscope, a bead having a correctly positioned and stretched out DNA strand was observed.

The STM probe was moved under control of a videocamera allowing visualization of the tip of the probe near the surface of the support, and the zone containing said bead was thus located.

After a rapid scanning, an area within said zone, containing regularly arranged nucleotides, was analyzed.

The STM topological analysis of the selected area was performed under the following conditions:

12 observation field: 10 nm×10 nm.

512 pixels per line scanning rate: 1 line/second.

Said topological analysis permitted to identify the following sequence bases (Pu: purin; Py: pyrimidlne):

Pu Py Py Pu Py Py.

Concurrently, electronic spectrum analysis of C=O or C—NH$_2$ groups permitted to distinguish between A and G (purine bases) and between C and T (pyrimidine bases), and the sequence was found to be:

A C C G T T (Seq. No.2).

---

---

I claim:

1. A method for arranging a polynucleotide sample on the surface of a substrate for point-by-point analysis of each successive base of said polynucleotide, said point-by-point analysis being performed by scanning said surface by means of a probe which is part of a tunnel effect microscope and which is capable of detecting a difference of level with respect to the surface of less than one atomic diameter, comprising:

positionning said polynucleotide by anchoring said polynucleotide towards a first extremity thereof to the substrate at a precise location on said substrate, and stretching out said anchored polynucleotide by performing at least one step selected from the group consisting of:

(i) placing the said anchored polynucleotide in a current of a fluid, and
(ii) applying an electric field.

2. The method of claim 1, where said polynucleotide at said first extremity and said substrate at said location bear first and second functional groups, respectively, said first and second functional groups being capable of mutually interacting when contacted, and wherein said anchoring comprises bringing into contact said functional groups to anchor said polynucleotide to said substrate.

3. The method of claim 2, wherein said functional groups interact electrostatically.

4. The method of claim 2, wherein said functional groups interact to form a covalent bond.

5. The method of claim 1, wherein the second extremity of said polynucleotide bears a functional group carrying an electric charge, and wherein the stretching out step comprises applying an electric field.

6. The method of claim 1, wherein said polynucleotide is initially double-stranded and is rendered single-stranded before performing said point-by-point analysis.

7. The method of claim 1, wherein said polynucleotide comprises a predetermined sequence synthesized at one end of the polynucleotide to be analyzed, whereby said first extremity comprises the free end of said predetermined sequence.

8. The method of claim 2, wherein said polynucleotide comprises a predetermined sequence synthesized at one end of the polynucleotide to be analyzed, whereby said first extremity comprises the free end of said predetermined sequence.

9. The method of claim 7, wherein said polynucleotide is initially double-stranded, said predetermined sequence is one which allows specific severance of one of the strands with a restriction enzyme, and wherein said enzyme is caused to act on said anchored polynucleotide to render it single-stranded.

10. The method of claim 1, comprising anchoring and stretching out said polynucleotide in a groove formed on said substrate.

11. The method of claim 1, wherein said location is defined by markings on the substrate.

* * * * *